United States Patent [19]

Bozarth

[11] 4,334,916
[45] Jun. 15, 1982

[54] USE OF N-CYCLOPROPYL-N'-(2-FLUOROPHENYL) UREA AS A SELECTIVE HERBICIDE

[75] Inventor: Gene A. Bozarth, Modesto, Calif.

[73] Assignee: Shell Oil Company, Houston, Tex.

[21] Appl. No.: 120,219

[22] Filed: Feb. 11, 1980

[51] Int. Cl.³ ............................................. A01N 47/30
[52] U.S. Cl. ........................................ 71/120; 564/54
[58] Field of Search ........................................... 71/120

[56] References Cited

U.S. PATENT DOCUMENTS 3,734,961  5/1973  Engelhart ............................. 71/120

FOREIGN PATENT DOCUMENTS 849570  6/1977  Belgium .

Primary Examiner—Catherine L. Mills

[57] ABSTRACT

N-cyclopropyl-N'-(2-fluorophenyl)urea, is used to selectively control weeds in plantings of grain sorghum.

1 Claim, No Drawings

USE OF N-CYCLOPROPYL-N'-(2-FLUOROPHENYL)UREA AS A SELECTIVE HERBICIDE

DESCRIPTION OF THE INVENTION

It has been found that N-cyclopropyl-N'-(2-fluorophenyl)urea, described by the formula

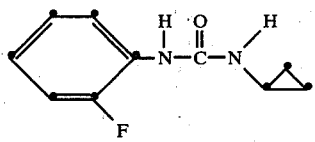

effectively controls weeds in grain sorghum plantings without significant injury to the sorghum plants.

To save repetition of its chemical name, the compound of this invention will be referred to henceforth herein as Compound I.

Compound I has been prepared as follows:

26.5 g (0.38 mole) of cyclopropylamine was added drop-by-drop over a 30-minute period to a solution of 50 g (0.365 mole) of o-fluorophenyl isocyanate in one liter of toluene. Reaction was immediate and exothermic, the temperature of the mixture rising from 25° C. to 50° C. during the addition. The resulting slurry was stirred for two hours at room temperature and filtered. The filter cake was washed with 150 ml of hexane and air dried to give 70 g of Compound I (93.5% yield, based on the isocyanate), mp: 118°–120° C. The identity of the compound was confirmed by appropriate analyses.

Compound I has been found to be useful for inhibiting growth of unwanted plants, being active with respect to both broad-leaved plants and grasses, and being effective when applied either preemergence (applied to the soil before the seeds have sprouted) or postemergence (applied to the foliage of the growing plants). It is somewhat more effective with respect to broad-leaved species of plants than with respect to grassy plants.

At the dosages that have effectively controlled unwanted plants, Compound I has not caused significant injury to grain sorghum plants.

For application to the locus to be treated, Compound I preferably is formulated with a carrier, or a surface-active material, or both.

By "carrier" is meant a solid or a fluid material, which may be inorganic or organic and of synthetic or natural origin, with which the active compound is mixed or formulated to facilitate its application to the plant, seed, soil or other object to be treated, or its storage, transport or handling.

Suitable solid carriers are natural and synthetic clays and silicates, for example, natural silicas such as diatomaceous earths; magnesium silicates, for example, talcs, magnesium aluminum silicates, for example, attapulgites and vermiculites; aluminum silicates, for example, kaolinites, montmorillonites and micas; calcium carbonates; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; solid polychlorophenols; bitumen, waxes such as, for example, beeswax, paraffin wax, and chlorinated mineral waxes; and solid fertilizers, for example, superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquified normally vaporous gaseous compounds. Mixtures of different liquids are often suitable. The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3–10% by weight of a dispersing agent, 15% of a surface-active agent and where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing ½–10% by weight of toxicant. Granules are usually prepared to have a size between 10 and 100 BS mesh (1.676–0.152 mm), and may be manufactured by agglomeration or impregnation techniques. Generally, granules will contain ½–25% by weight toxicant and 0–1% by weight of additives such as stabilizers, slow release modifiers and binding agents. Emulsifiable concentrates usually contain, in addition to the solvent and, when necessary, cosolvent, 10–50% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight toxicant, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate with water, also are suitable. The said emulsions may be of the water-in-oil or of the oil-in-water type, and may have a thick mayonnaise-like consistency.

The compositions may also contain other ingredients, for example, other compounds possessing pesticidal, especially insecticidal, acaricidal, herbicidal or fungicidal properties.

Protection of a locus or area from undesirable plants is effected by applying Compound I, ordinarily in a composition of one of the aforementioned types, to the foliage of the plants or plant growth medium, e.g., soil in which the plant is growing or in which the seeds are present. The active compound, of course, is applied in amounts sufficient to exert the desired action.

The amount of Compound I to be used in controlling undesirable vegetation will naturally depend on the condition of the vegetation, the degree of activity desired, the formulation used, the mode of application, the climate, the season of the year, and other variables. Recommendations as to precise amounts are, therefore, not possible. In general, however, application to the locus to be protected of from 0.1 to 10.0 kilograms per hectare of Compound I will be satisfactory.

EXAMPLES OF HERBICIDAL ACTIVITY

In the following examples, the species of plants that were tested were:
Barnyard grass (watergrass)—*Echinochloa crus-galli*
Crabgrass—*Digitaria sanguinalis*
Downy brome—*Bromus tectorum*
Giant foxtail—*Setaria faberii*
Wild oats—*Avena fatua*
Yellow foxtail—*Setaria lutescens*
Hemp sesbania (coffeeweed)—*Sesbania exaltata*
Jimsonweed—*Datura stramonium*
Ivyleaf morningglory—*Ipomoea hederacea*
Mustard—*Brassica kaber*
Redroot pigweed—*Amaranthus retroflexus*
Prickly sida—*Sida spinosa*
Sicklepod—*Cassia obtusifolia*
Velvetleaf—*Abutilon theophrasti*
Garden cress—*Lepidium sativum*
Grain sorghum—*Sorghum vulgare* (Pioneer 265)
Corn—*Zea maize* (deKalb X363)
Cotton—*Gossypium hirsutum* (Acala SJ-2)
Rice—*Oryza sativa* (Calrose)
Soybean—*Glycine max* (Amsoy 71)
Wheat—*Triticum aestivum* (Cajeme 71)
Sugar beet—*Beta vulgaris*
Cocklebur—*Xanthum pennsylvanicum*
Lambsquarters—*Chenopodium album*
Johnsongrass—*Sorghum halopense*

EXAMPLE 1

The preemergence herbicidal activity of Compound I was evaluated by planting seeds of barnyard grass, garden cress, downy brome, velvetleaf, yellow foxtail, and sicklepod in test tubes, nominally measuring 25×200 millimeters, filled about three-quarters full of untreated soil, in each case covered on top with about 2.5 cubic centimeters of soil treated with the test compound at the rates of 0.1 and 1 milligram respectively, Table I at Rates I and II, respectively. The dosages of test compound were approximately two and twenty pounds of test compound per acre, respectively. The seeds were planted in the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
| --- | --- |
| 9 | No living tissue |
| 8 | Living tissue, but plant expected to die |
| 7 | Plant badly damaged, but expected to live |
| 6 | Plant badly damaged, but expected to recover completely |
| 5 | Unacceptable damage for crop plants, insufficient damage to weeds |
| 3-4 | Definite damage |
| 1-2 | Plant slightly affected, possibly by the chemical, possibly due to biological variability |
| 0 | No visible effect |

The postemergence activity of Compound I was evaluated by spraying 10-day old large crabgrass plants, 13-day old redroot pigweed plants, 6-day old downy brome plants, 9-day old velvetleaf plants, 9-day old yellow foxtail plants and 9-day old sicklepod plants to runoff with a liquid formulation of the test compound at the rates of 2.4 milliliters of a 0.025% solution (about one pound of Compound I per acre), designated Rate I in Table I, and 2.4 milliliters of a 0.25% solution (about ten pounds of Compound I per acre), designated Rate II in Table I. The sprayed plants were held under controlled conditions of temperature, moisture and light for 7 to 8 days and the effect of Compound I was then evaluated visually, the results being rated on the 0 to 9 scale described above.

The results of the tests are summarized in Table I.

TABLE I

| | Preemergence (Soil) | | | | | | | | | | | | Postemergence (Foliar) | | | | | | | | | | | |
| --- | --- | --- | --- | --- | --- | --- | --- | --- | --- | --- | --- | --- | --- | --- | --- | --- | --- | --- | --- | --- | --- | --- | --- | --- |
| | Barnyard Grass | | Garden Cress | | Downy Brome | | Velvetleaf | | Yellow Foxtail | | Sicklepod | | Crabgrass | | Pigweed | | Downy Brome | | Velvetleaf | | Yellow Foxtail | | Sicklepod | |
| | Dosage | | | | | | | | | | | | | | | | | | | | | | | |
| Compound | I | II | I | II | I | II | I | II | I | II | I | II | I | II | I | II | I | II | I | II | I | II | I | II |
| I | 7 | 8 | 9 | 9 | 6 | 7 | 9 | 9 | 3 | 7 | 7 | 7 | 5 | 9 | 7 | 9 | 6 | 9 | 8 | 9 | 9 | 9 | 9 | 9 |

EXAMPLE 2

The preemergence herbicidal activity of Compound I was further determined with respect to several common species of weeds, by spraying a formulation of the compound on the soil in which seeds of the weeds had been sown. In each series of tests, the plants were grown in narrow trays and sprayed with the test compound. The solution of the test compound was sprayed over the tray, from one end to the other, the concentration of the test compound in the formulation varying log-arithmically from a higher value (5 pounds of Compound I per acre) at one end of the band to a lower value (0.55 pound of Compound I per acre) at the other end of the band. The effect of the test compound was evaluated visually and reported as the nominal rate of application, in pounds of Compound I per acre of soil band, at which 90% inhibition of the growth of the weeds occurred, this being referred to as the 90% growth inhibition, or $GID_{90}$, dosage. Results of the test, as well as the weed species involved, are set out in Table II.

TABLE II

| | Barnyard Grass | Downy Brome | Yellow Foxtail | Crab-grass | Velvet-leaf | Mustard | Pig-weed | Sicklepod |
|---|---|---|---|---|---|---|---|---|
| $GID_{90}$ | −0.55[a] | −0.55 | −0.55 | −0.55 | −0.55 | −0.55 | −0.55 | −0.55 |

[a]The symbol "−" means "less than".

EXAMPLE 3

The postemergence herbicidal activity of Compound I was further determined with respect to several common species of weeds, by spraying a formulation of the compound on the foliage of young growing weeds. In each series of tests, the plants were grown in narrow trays and sprayed with the formulation. The formulation of Compound I was sprayed over the tray, from one end to the other, to run-off, the concentration of Compound I in the formulation varying logarithmically from a higher value (5 pounds per acre) at one end of the series to a lower value (0.55 pound per acre) at the other end of the series. The effect of Compound I was evaluated visually and reported as the nominal rate of application, in pounds Compound I per acre, at which 90% inhibition of the growth of the weeds occurred, this being referred to as the 90% growth inhibition or $GID_{90}$ dosage. Results of the test, as well as the weed species involved, are set out in Table III.

TABLE III

| | Barnyard Grass | Downy Brome | Yellow Foxtail | Crab-grass | Velvet-leaf | Mustard | Pig-weed | Sicklepod |
|---|---|---|---|---|---|---|---|---|
| $GID_{90}$ | 4.1 | +5.0[a] | 4.5 | −0.55 | −0.55[a] | −0.55 | −0.55 | −0.55 |

[a]The symbol "+" means "more than", the symbol "−" means "less than".

EXAMPLE 4

The pre- and postemergence activity of Compound I was further determined with respect to a number of crop plants and common species of weeds, using the procedure described in Examples 2 and 3, except that the test compound was applied at three different fixed dosages of Compound I per acre, and the results were evaluated with reference to the 0–9 scale described in Example 1. The results of the tests are reported in Table IV.

TABLE IV

| Plant Species | Rating of Effect at Indicated dosage (lb/acre) | | | | | |
|---|---|---|---|---|---|---|
| | Preemergence | | | Postemergence | | |
| | 0.25 | 0.50 | 1.0 | 0.5 | 1.0 | 2.0 |
| Corn | 2 | 5 | 7 | 0 | 0 | 0 |
| Cotton | 4 | 8 | 9 | 4 | 5 | 6 |
| Rice | 5 | 6 | 7 | 0 | 2 | 2 |
| Grain Sorghum | 2 | 2 | 5 | 2 | 2 | 2 |
| Soybean | 9 | 9 | 9 | 5 | 5 | 8 |
| Sugar beet | 9 | 9 | 9 | 5 | 9 | 9 |
| Wheat | 7 | 8 | 8 | 0 | 0 | 2 |
| Barnyard Grass | 9 | 9 | 9 | 2 | 0 | 2 |
| Crabgrass | 9 | 9 | 9 | 5 | 7 | 7 |
| Downy Brome | 9 | 9 | 9 | 0 | 2 | 2 |
| Giant Foxtail | 5 | 9 | 9 | — | — | — |
| Johnsongrass | 3 | 7 | 9 | 0 | 2 | 2 |
| Wild Oats | 9 | 9 | 9 | 0 | 2 | 2 |
| Yellow Foxtail | 9 | 9 | 9 | — | — | — |
| Cocklebur | 9 | 9 | 9 | 4 | 5 | 6 |
| Hemp sesbania (Coffeeweed) | 9 | 9 | 9 | 4 | 6 | 6 |
| Jimsonweed | 9 | 9 | 8 | 5 | 9 | 9 |
| Lambsquarters | 9 | 9 | 9 | 7 | 9 | 9 |
| Morningglory | 6 | 9 | 9 | 4 | 6 | 9 |
| Mustard | 9 | 9 | 9 | 7 | 7 | 9 |
| Pigweed | 9 | 9 | 9 | 9 | 9 | 9 |
| Prickly sida | 9 | 9 | 9 | 0 | 0 | 9 |
| Sicklepod | 9 | 9 | 9 | 4 | 9 | 9 |
| Velvetleaf | 9 | 9 | 9 | 9 | 9 | 9 |

It will be noted that from these tests, Compound I selectively controls the weed species in plantings of grain sorghum.

EXAMPLE 5

The tests described in Example 2 were repeated, to compare the activity of Compound I with respect to grain sorghum and certain weed species, the lower dosage used being 0.06 pound per acre of Compound I. The dosages of Compound I, pounds per acre, required to inhibit growth by 10% ($GI_{10}$) and 90% ($GI_{90}$) were determined. The results are reported in Table V.

TABLE V

| | Plant Species | | | | | | | |
|---|---|---|---|---|---|---|---|---|
| | Grain Sorghum | | Pigweed | Velvetleaf | Crabgrass | Downy Brome | Barnyard Grass | Johnsongrass |
| | Dosage | | | | | | | |
| Compound | $GI_{10}$ | $GI_{90}$ | $GI_{90}$ | $GI_{90}$ | $GI_{90}$ | $GI_{90}$ | $GI_{90}$ | $GI_{90}$ |
| I | 1.5 | 2.1 | −0.55[a] | −0.06 | 0.13 | 0.16 | 0.55 | 0.55 |

[a]The symbol "−" means "less than".

EXAMPLE 6

The tests described in Example 3 were repeated, to compare the activity of Compound I with respect to grain sorghum and certain weed species, the lower dosage used being 0.06 pound per acre of Compound I.

The dosages of Compound I, pounds per acre, required to inhibit growth by 10% ($GI_{10}$) and 90% ($GI_{90}$) were determined. The results are reported in Table VI.

TABLE VI

| | Plant Species | | | | | | |
|---|---|---|---|---|---|---|---|
| | Grain Sorghum | Yellow Foxtail | Velvetleaf | Crabgrass | Downy Brome | Barnyard Grass | Johnsongrass |
| | | | | Dosage | | | |
| Compound | $GI_{10}$   $GI_{90}$ | $GI_{90}$ | $GI_{90}$ | $GI_{90}$ | $GI_{90}$ | $GI_{90}$ | $GI_{90}$ |
| I | 0.6[a]  +5.0[a] | 1.0 | −0.55[a] | −0.55 | 1.7 | 1.9 | 2.8 |

[a] The symbol "+" means "more than"; the symbol "−" means "less than".

I claim:

1. A method for controlling weeds in a planting of grain sorghum which comprises applying to the locus an effective dosage of N-cyclopropyl-N'-(2-fluorophenyl)urea.

* * * * *